(12) United States Patent
Hering et al.

(10) Patent No.: US 10,252,237 B2
(45) Date of Patent: Apr. 9, 2019

(54) SUSTAINED SUPER-SATURATIONS FOR CONDENSATIONAL GROWTH OF PARTICLES

(71) Applicant: Aerosol Dynamics Inc., Berkeley, CA (US)

(72) Inventors: Susanne Vera Hering, Berkeley, CA (US); Steven Russel Spielman, Oakland, CA (US); Gregory Stephen Lewis, Berkeley, CA (US)

(73) Assignee: Aerosol Dynamics Inc., Berkeley, CA (US)

( * ) Notice: Subject to any disclaimer, the term of this patent is extended or adjusted under 35 U.S.C. 154(b) by 644 days.

(21) Appl. No.: 14/886,661

(22) Filed: Oct. 19, 2015

(65) Prior Publication Data

US 2016/0107137 A1    Apr. 21, 2016

Related U.S. Application Data

(60) Provisional application No. 62/215,585, filed on Sep. 8, 2015, provisional application No. 62/065,645, filed on Oct. 18, 2014.

(51) Int. Cl.
*B01D 53/00* (2006.01)
*B01J 8/08* (2006.01)
(Continued)

(52) U.S. Cl.
CPC ............ *B01J 8/087* (2013.01); *B01D 5/0006* (2013.01); *G01N 15/065* (2013.01);
(Continued)

(58) Field of Classification Search
None
See application file for complete search history.

(56) References Cited

U.S. PATENT DOCUMENTS 6,330,060 B1 *   12/2001   Flagan ............... G01N 15/0211
                                                         250/335
6,712,881 B2      3/2004   Hering et al.
(Continued)

FOREIGN PATENT DOCUMENTS

CN        102053048 A    5/2011
CN        103084123 A    5/2013
(Continued)

OTHER PUBLICATIONS

Lewis et al., "Minimizing Concentration Effects in Water-Based, Laminar-Flow Condensation Particle Counters", Aerosol Science and Technology, 47: 645-654, Feb. 2013, Berkeley, California, USA.

(Continued)

*Primary Examiner* — Amber R Orlando
*Assistant Examiner* — Phillip Y Shao
(74) *Attorney, Agent, or Firm* — Vierra Magen Marcus LLP

(57) ABSTRACT

An apparatus and method for creating enlarged particles in a flow. The apparatus includes a coiled tube having a tube diameter and a coil diameter, the tube having an input receiving the flow and an output, the tube having a length between the input and the output. A heater heats a first portion of the tube along a first, longitudinal portion of the tube, and a cooler cools a second, longitudinal portion of the tube along at least a second portion of the tube. The method includes heating a first portion of the tube along a first longitudinal portion of the tube, and simultaneously cooling a second portion of the tube along at least a second longitudinal portion of the tube. While heating and cooling, the method includes introducing a flow into an interior of the tube at an input, the flow moving the output.

8 Claims, 14 Drawing Sheets

(51) Int. Cl.
B01D 5/00 (2006.01)
G01N 15/06 (2006.01)

(52) U.S. Cl.
CPC ............. *B01J 2208/00026* (2013.01); *B01J 2208/00203* (2013.01); *G01N 2015/0681* (2013.01)

(56) References Cited

U.S. PATENT DOCUMENTS

| | | | |
|---|---|---|---|
| 8,465,791 B2 | 6/2013 | Liu et al. | |
| 8,801,838 B2 | 8/2014 | Hering et al. | |
| 2003/0082825 A1* | 5/2003 | Lee ................... | G01N 15/0255 436/148 |
| 2008/0083274 A1 | 4/2008 | Hering | |
| 2009/0009749 A1* | 1/2009 | Ahn ................... | G01N 15/065 356/37 |
| 2011/0121093 A1* | 5/2011 | Jarrell ................. | G01N 30/84 239/13 |
| 2016/0033384 A1* | 2/2016 | Bergmann ........... | G01N 15/065 73/28.01 |

FOREIGN PATENT DOCUMENTS

| | | |
|---|---|---|
| CN | 103328951 B | 4/2017 |
| WO | WO03065005 A2 | 8/2003 |
| WO | 2005066610 A1 | 7/2005 |
| WO | 2011047219 A2 | 4/2011 |

OTHER PUBLICATIONS

Hering et al., "A Laminar-Flow, Water-Based Condensation Particle Counter (WCPC)", Aerosol Science and Technology, 39:659-672, Jan. 2005.
Eiguren-Fernandez et al., "Time-Resolved Characterization of Particle Associated Polycyclic Aromatic Hydrocarbons Using a Newly-Developed Sequential Spot Sampler With Automated Extraction and Analysis" Atmospheric Environment 96,125-134, Oct. 2014, Berkeley, CA, USA.
Hering et al., "Moderated, Water-Based, Condensational Particle Growth in a Laminar Flow", Aerosol Science and Technology, 48:401-408, Jan. 2014, Berkeley, CA, USA.
Heist et al., "Investigation Of The Homogeneous Nucleation Of Water Vapor Using A Diffusion Cloud Chamber", The Journal of Chemical Physics 59, 665, Jan. 1973.
Hudon et al., "An Improved Continuous Flow Diffusion Cloud Chamber", Journal of Applied Meteorology, vol. 15, Apr. 1976.
Bertelsmann et al., "Two-Dimensional Transport And Wall Effects In The Thermal Diffusion Cloud Chamber. II. Stability of Operation", J. Chem. Phys. 106 (2), Jun. 1996.
Peter H. McMurry, "The History of Condensation Nucleus Counters", Aerosol Science and Technology 33: 297-322, Oct. 2000.
Squires et al., "A Comparison of Cloud Nucleus Measurements over Central North America and the Caribbean Sea", Journal of the Atmospheric Sciences, Jul. 1966.
James G. Hudson, "Relationship Between Fog Condensation Nuclei and Fog Microstructure", American Meterological Society, Aug. 1980.
James G. Hudson, "An Instantaneous CCN Spectrometer", Journal of Atmospheric and Oceanic Technology, Dec. 1989.
Eiguren Fernandez et al., "Design and Laboratory Evaluation of a Sequential Spot Sampler for Time-Resolved Measurement of Airborne Particle Composition", Aerosol Science and Technology, 48: 655-663, Mar. 2014.
Hering et al., "A Method for Particle Size Amplification by Water Condensation in a Laminar, Thermally Diffusive Flow", Aerosol Science and Technology, 39: 428-436, Mar. 2005.
Katz et al., "Diffusion Cloud—Chamber Investigation of Homogeneous Nucleation", The Journal of Chemical Physics vol. 47, No. 2, Jul. 1967.
Pui et al., "A Compact Coiled Denuder for Atmospheric Sampling", Environ. Sci. Technol., vol. 24, No. 3, Mar. 1990.
Stolzenburg et al., "An Ultrafine Aerosol Condensation Nucleus Counter", Aerosol Science and Technology 14: 48-65, Mar. 1990.
Dravid et al., "Effect of Secondary Fluid Motion on Laminar Flow Heat Transfer in Helically Coiled Tubes", AIChE Journal (vol. 17, No. 5), Sep. 1971.
Alofs et al., "A Vindication of the Twomey-Type Cloud Condensation Nucleus Counter", Journal of Atmospheric and Oceanic Technology, Sep. 1986.
International Preliminary Report on Patentability dated Apr. 27, 2017, in International Patent Application No. PCT/US2015/056234 filed Oct. 19, 2015.
International Search Report and Written Opinion dated Jan. 27, 2016, in International Patent Application No. PCT/US2015/056234 filed Oct. 19, 2015.
Chinese Office Action dated Nov. 2, 2018, Chinese Patent Application No. 2015800696256.

\* cited by examiner

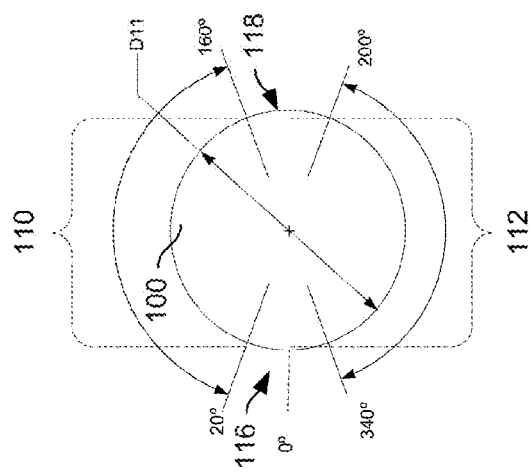
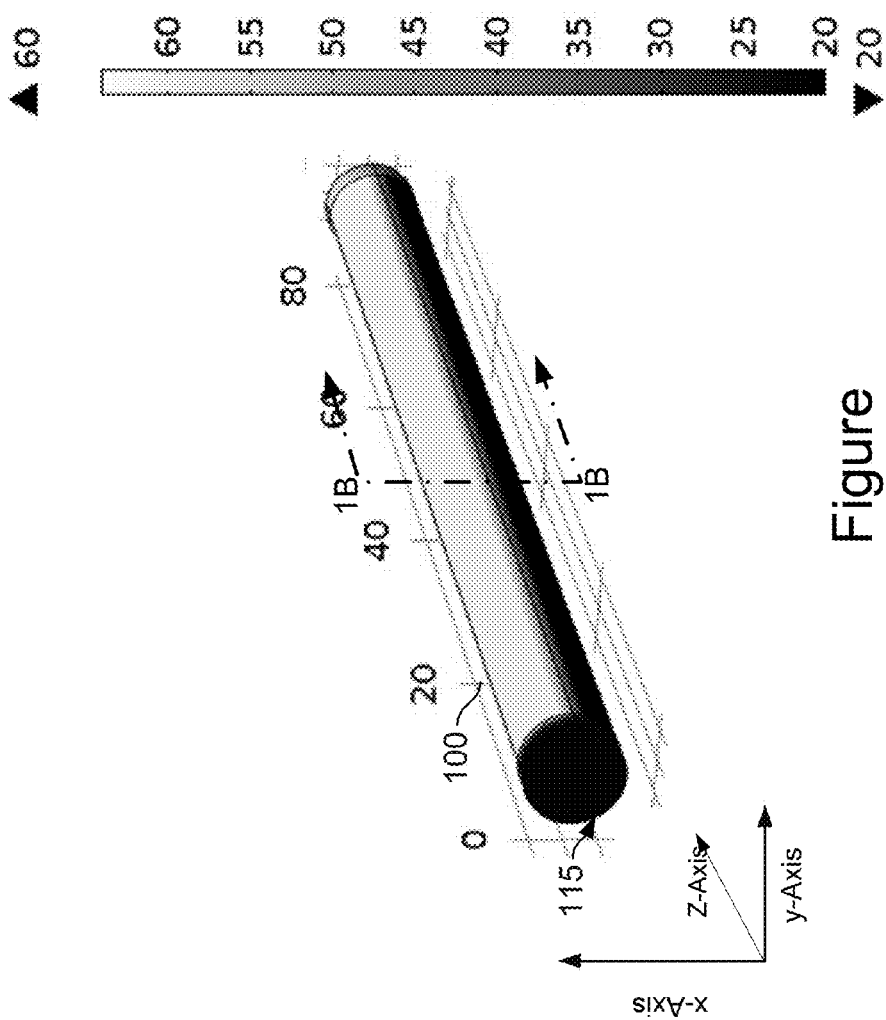
Figure 1B
Figure 1A

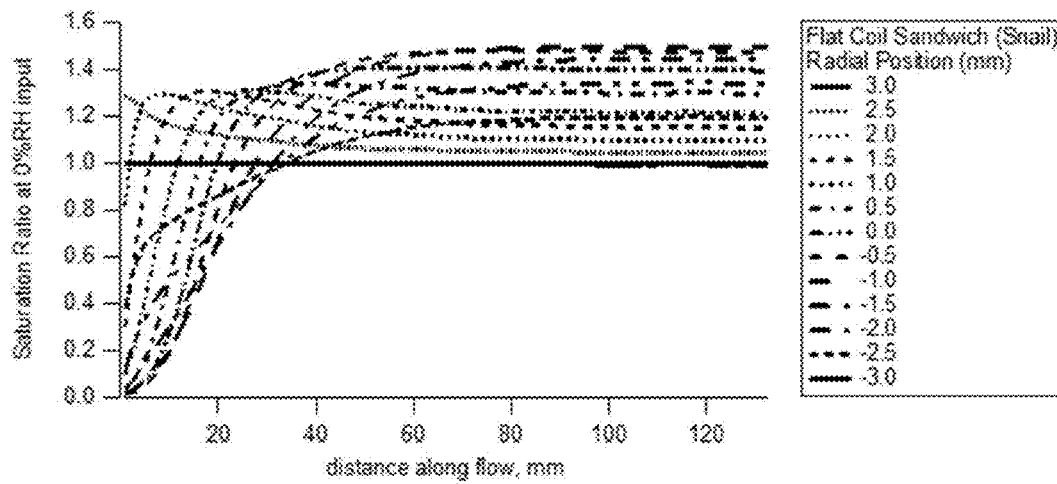
Figure
7A
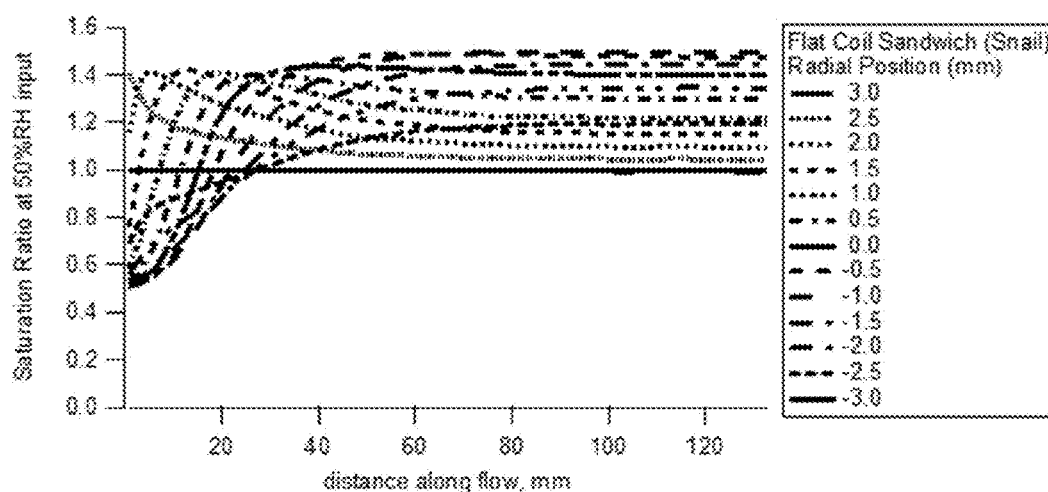
Figure
7B

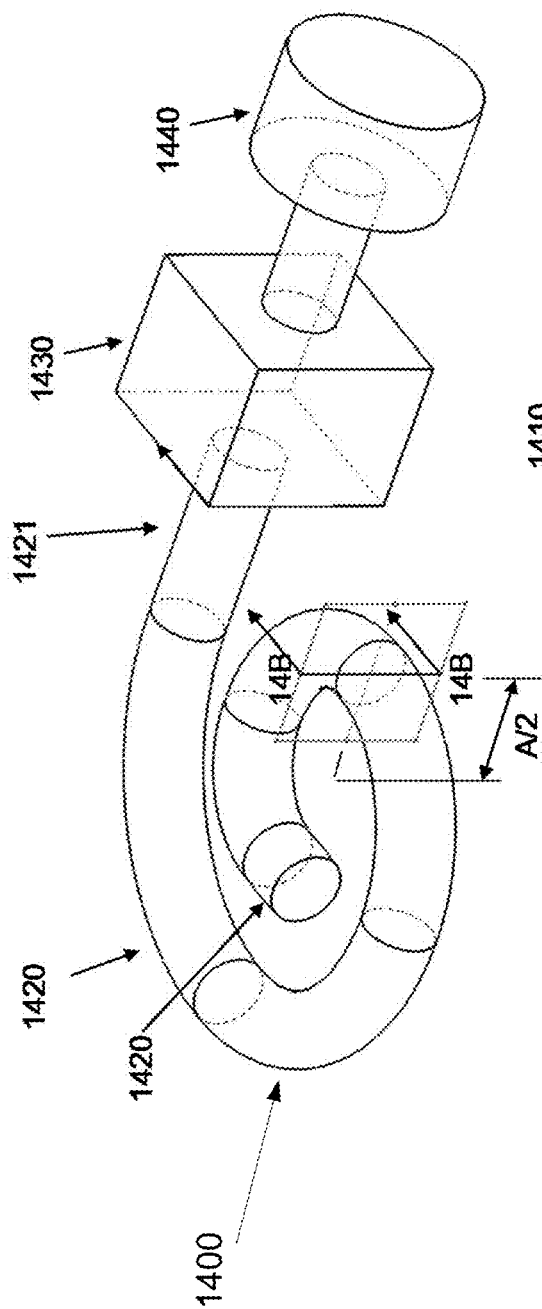
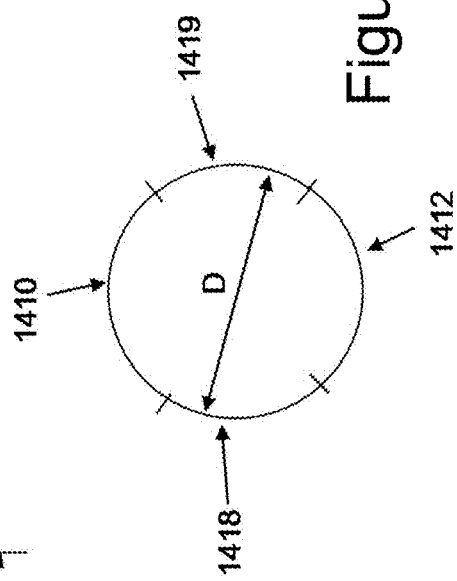
Figure 14A
Figure 14B

SUSTAINED SUPER-SATURATIONS FOR CONDENSATIONAL GROWTH OF PARTICLES

CLAIM OF PRIORITY

This application claims priority to U.S. Provisional application 62/065,645 filed 18 Oct. 2014 "A Coiled Growth tube for Water Condensation onto Ultrafine Particles" and U.S. Provisional application 62/215,585 filed 8 Sep. 2015 "Method of Providing Sustained Super-Saturations for Condensational Growth of Particles."

BACKGROUND

Condensational growth systems have been used to enlarge sub micrometer sized aerosolized particles to form droplets. These aerosolized particles may be airborne, or carried by another process gas such as nitrogen, but are defined as particles of condensed matter (liquid or solid) suspended in a gas that is too small to settle by gravity in the time scales of interest. Often the aerosolized particles of interest are less than a few micrometers in diameter. To facilitate their measurement, these particles may be grown through condensation to form larger droplets that can be detected or manipulated much more easily than the original particle. For example, the droplets can be detected optically, captured inertially, or focused aerodynamically.

For small particles, the initiation of condensational growth is created by exposure of the particle to a region of vapor super-saturation, defined as a region in which the vapor pressure of the condensing vapor is higher than its saturation value over a flat surface. These supersaturated conditions are used because the equilibrium vapor pressure above the curved surface of an ultrafine particle is higher than over a flat surface of the same chemical composition. This is due to the energy associated with the surface tension, a phenomenon described by the Kelvin relation. Water condensation onto small particles requires relative humidity values in excess of 100%. Roughly speaking, the relative humidity needed to activate the condensational growth of particles below 6 nm in diameter is in the range of 140% and larger. The exact value of the super-saturation required also depends on particle chemistry, which for soluble salts is described by the Kohler relations.

It is not possible to have super-saturated conditions at walls of the container carrying the flow, as any excess water vapor will simply deposit on the walls. However, it is possible to create non-equilibrium conditions within the core of the flow, thereby temporarily providing supersaturated conditions. Methods of achieving this include (1) adiabatic expansion of a saturated flow, (2) the rapid (generally turbulent) mixing of flows of differing temperatures, and (3) laminar flow diffusion wherein a cooler flow is introduced into a warm, wet-walled tube.

With each of these methods the time that the flow experiences supersaturated conditions is limited. For example, with the laminar flow methods the supersaturation profiles exhibit a sharp maximum, and then decay. As most of the condensational growth occurs in this peak supersaturation region, this limited time also limits the size of the droplet that is formed. This is especially an issue when operating at low supersaturations, such as is typical of clouds. Also, the activation of condensational growth can be kinetically limited, such that this short supersaturation is insufficient to initiate condensational growth on those particles that are hydrophobic, i.e. that have an inherent low probability for water molecules to adhere to their surface.

SUMMARY

The technology, briefly described includes a apparatus and method for creating enlarged particles in a flow. The apparatus includes a coiled tube having a tube diameter and a coil diameter, the tube having an input receiving the flow and an output, the tube having a length between the input and the output. A heater is configured to heat a first longitudinal portion of the tube along a first portion of the tube diameter, the first portion of the tube diameter having an approximately constant position relative to a cross section of the tube along the length of the tube. A cooler configured to cool a second logitudinalportion of the tube along at least a second portion of the tube diameter, the second portion of the tube diameter being at an approximately constant position along the length of the tube. The coiled tube includes interior walls adapted to be wetted with a condensing fluid throughout.

The method includes providing a coiled tube having a tube diameter and a coil diameter, the tube having an input receiving an input flow and an output, the tube having a length between the input and the output. The method thereafter includes heating a first longitudinal portion of the tube along a first portion of the tube diameter, the first portion of the tube diameter having a constant position along the length of the tube, and simultaneously cooling a second longitudinal portion of the tube along at least a second longitudinal portion of the tube diameter, the second portion of the tube diameter being at a constant position along the length of the tube. While heating and cooling, the method includes introducing a flow into an interior of the tube at an input, the flow moving to the output.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

FIG. 1A illustrates a first embodiment of an apparatus in accordance with the present technology comprising a straight growth tube.

FIG. 1B illustrates a cross-section of the straight growth tube along line 1B-1B.

FIG. 2 illustrates the saturation ratio for a slice of the flow within the straight growth tube of FIG. 1 in operation.

FIGS. 3A and 3B are graph illustrating the saturation ratio at several radial positions from a vertical slice of a 0.3 L/min flow of air in the device of FIG. 1A for 50% RH and 0% RH, respectively.

FIG. 4 illustrates a second embodiment of the technology wherein comprising a flat coil growth in a single plane, wherein the upper side is warmer than the underside.

FIG. 5 is a cross-section of the device of FIG. 4 illustrating the velocity fields the coil illustrating secondary flow patterns.

FIG. 6 illustrates the saturation ratio for a slice of the flow in the device of FIG. 4 extending between the warm and cold surfaces.

FIGS. 7A and 7B are graphs illustrating the saturation ratio at several radial positions from the vertical slice of FIG. 6 for a 0.3 L/min flow of air entering at 0% RH and 50% RH respectively.

FIG. 8A illustrates another embodiment of the technology comprising a helical growth tube, with a spiraling coil, wherein the inner side and outer sides of the coil are at different temperatures.

FIGS. 14A and 14B are a perspective and cross-sectional view of a general apparatus formed in accordance with the present technology, showing an inlet, a coiled growth tube, an outlet, a droplet measuring or manipulation device, and a pump, blower or other flow mover.

DETAILED DESCRIPTION

Technology is presented which relates to a method of enlarging airborne particles by condensational growth by water or other vapor, to form droplets that may be readily detected optically, captured inertially or focused aerodynamically.

A growth tube structure and method of operating a growth tube are provided. The method and apparatus of the present technology provide a "growth tube sandwich" of various configurations wherein flow travels in an axial direction down a wet-walled tube whose wall temperatures are varied with angular position, but are generally constant with axial position over a majority of the length of the tube. In this context, "constant" means that the angular position of the heated and cooled portions discussed herein may vary by one or several degrees, but remain within the upper or lower half of the tube cross-section along the length of the tube. For example, walls within the angular positions from around 20-160° (relative to a common origin) may be warm while those along the angular positions from around 200-340° (relative to a common origin at 0°), are cold. Intervening radial positions in regions (at, for example 0°±20° and 180°±20°) are transition regions with intermediate temperatures. This same angular wall temperature profile extends for most of the length of the tube, fixed for much of the axial distance. This tube may be configured as a straight tube, as a flat coil, or as a helix.

This configuration produces a region in the central portion of the flow where the local vapor pressure of the fluid with which the walls are wetted is higher than the fluid's equilibrium value at the local temperature. As the flow travels down the tube, the vapor pressure and temperature profiles approach a steady state condition, wherein the saturation ratio (defined as the ratio of vapor pressure to equilibrium vapor pressure) depends only on radial and angular positions, nearly independent of the axial position. These flow trajectories with nearly constant, high saturation ratio provide longer activation times, and more particle growth, than prior laminar flow methods. This approach is especially effective when the diffusivities of the condensing fluid and the thermal diffusivity of the carrier gas are similar, such as is the case of water condensation onto particles carried in air.

A first configuration of the growth tube apparatus in accordance with the present technology is a straight tube 100, as shown in FIG. 1A. A device configured to operate with the tube 100 of FIG. 1A may further include one or more input devices providing a flow to input end 115 and output devices coupled to an opposing end of the growth tube 100, examples of which are illustrated and described with respect to FIG. 11A-11D. It should be understood that the input and output devices of FIG. 11A-11D may be utilized with any of the growth tube apparatus embodiments described herein.

In FIG. 1A, dark and light shading indicates temperature variance, where lighter shading represents warmer temperatures and dark shading represents colder temperatures, in accordance with the scale shown on the right side of FIG. 1A.

The inner walls of the tube 100 are wetted with the condensing fluid throughout. As illustrated in FIGS. 1A and 1B, one side 110 of the tube 100 is warmer than the other side. In the illustration of FIG. 1A, 1B the wall in region 110 is held at 60° C. for angular positions of roughly 20° to 160°, and the wall in region 112 is held at 20° C. for angular positions of 200° to 340° in region 112 which extends an axial distance equal to, or greater than the volumetric flow rate multiplied by 0.5 s/cm$^2$. The angular positions are relative to a common origin at the center of the tube (indicated as 0° in FIG. 1B), and the angular positions (an origin), and hence regions 110 and 112, are constant over the length of the tube 100, thereby extending longitudinally along the length of the tube. It should be understood that a particle flow having an ambient temperature of about 22° C. may be introduced into the tube 100 via the input end 115 of the tube 100. Airflow enters at opening 115 the lower left and travels in the z-direction. The walls are wetted with the liquid phase of the condensing vapor throughout. Intervening radial positions in regions 116 and 118 (0±20° and 180±20°, respectively) may be provided as transition regions with intermediate temperatures.

In an alternative embodiment, region 110 may greater than 140° such that region 110 is up to half of the tube 100 and region 112 is likewise up to half of tube 100, with the transition regions 116 and 118 minimized.

Calculations were performed for the configuration of FIG. 1A-AB for the case of water condensation. The inner walls are wetted with water. The tube has an inner diameter D1 of 6 mm, and carries an air flow of 0.3 L/min. Under these conditions the flow is laminar and the transport is by convective diffusion. The temperature differences between the opposite sides of the tube creates a gradient in the temperature. Likewise there is a gradient in the vapor profile. Near the entrance 115 of the tube, the vapor pressure and temperature profiles evolve with axial position, as does the saturation ratio. Further down the tube, these parameters approach steady state values that are maintained for the remainder of the length of the tube.

In this near steady state region, the values of the saturation ratio near the centerline exceed one. These "supersaturated" conditions (i.e. saturation ratio greater than 1) result from the differences in the rates of vapor mass and heat transport from the walls into the flow, as well as the nonlinear dependence of the equilibrium vapor pressure on temperature.

Figure 2:
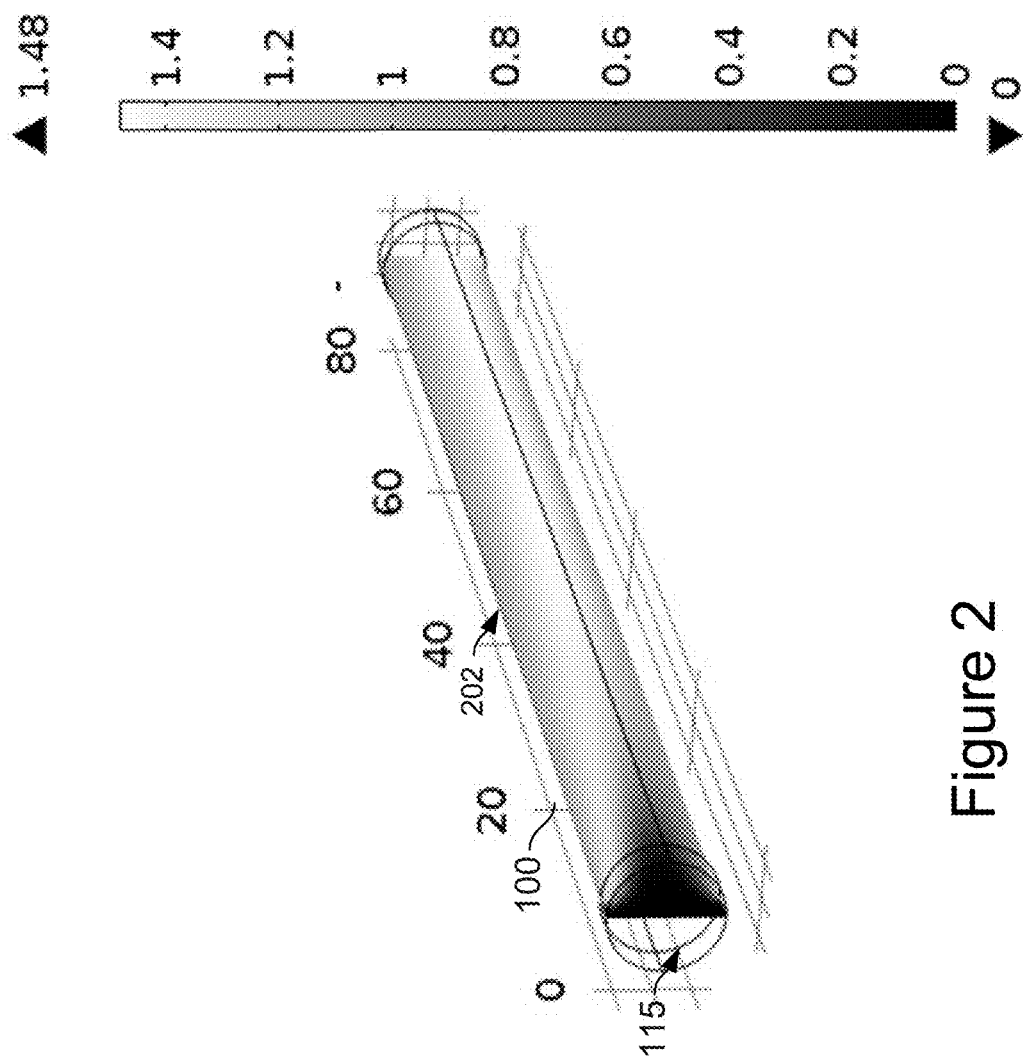
Figure 3A:
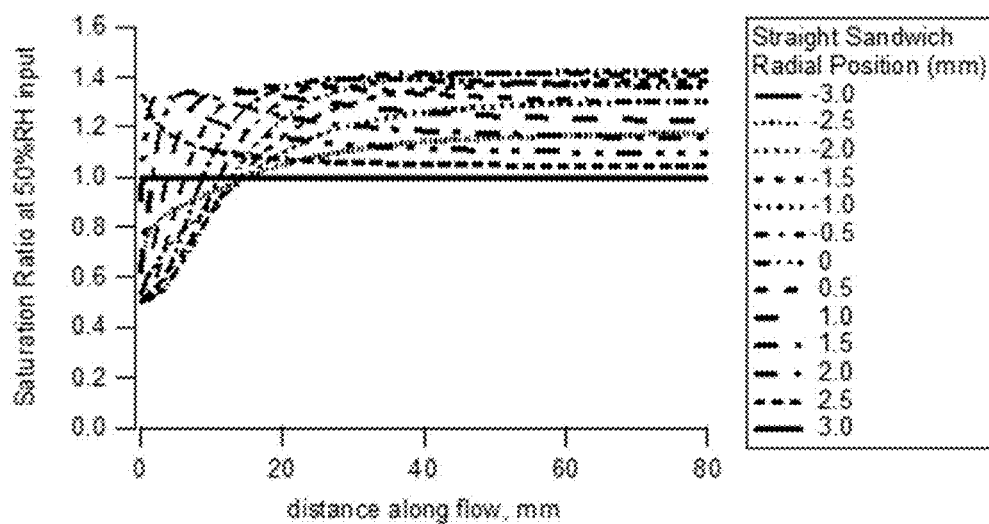
Figure 3B:
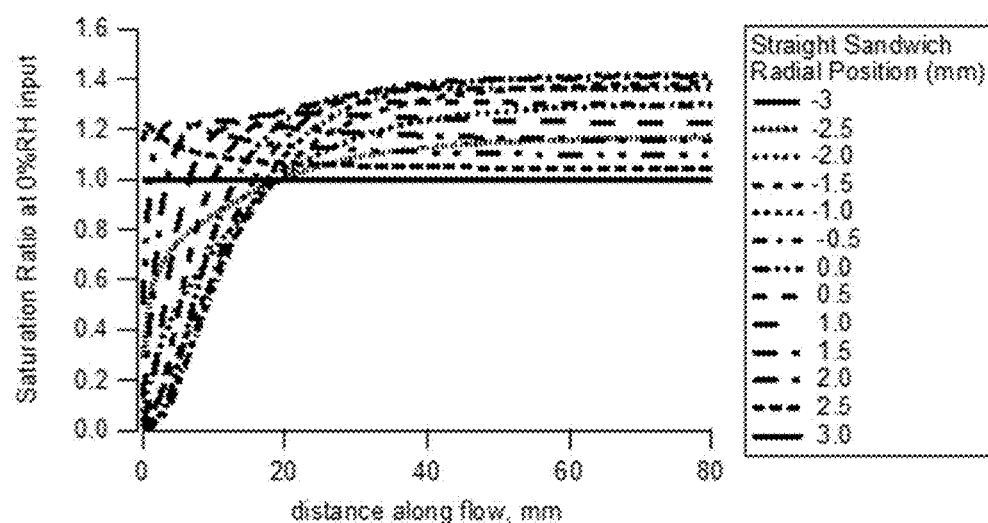

The saturation profiles calculated for FIG. 1A-AB are shown in FIGS. 2, 3A and 3B. FIG. 2 shows the saturation ratio for a slice 202 of the flow, the slice extending between the warm and cold surfaces of the growth tube of FIG. 1. The slice illustrated lies in the x-z plane at the y-axis position of y=0, and extends between the warm 110 and cold 112 surfaces of the growth tube of FIG. 1. In the slice, 202, higher saturation ratios are indicated by lighter shading, and low saturation ratio values are darker, in accordance with the scale to the right. The tube diameter is 6 mm and the flow is 0.3 L/min. The condensing vapor is water, the carrier gas is air, and the entering flow is at 22° C. and 50% RH.

As stated above, for the profiles of FIGS. 2, 3A and 3B, the tube diameter D1 is 6 mm, the flow is 0.3 L/min. The condensing vapor is water, the carrier gas is air, and the entering flow is at 22° C. and 50% relative humidity (RH). Along the slice shown in FIG. 2, the flow attains a maximum saturation ratio of 1.42. The maximum occurs at a distance of about one-sixth of one tube radius from the centerline, towards the colder wall.

FIG. 3A shows the axial dependence of the saturation ratio for several radial positions along the x-z plane positioned at y=0 of FIG. 2. The saturation ratio at the interior walls is always equal to 1, as the boundary conditions is for wetted walls, and any excess water vapor would simply condense. Saturation ratios in the core of the flow increase rapidly at the entrance 115 of the tube, rising first at large radial positions near the walls, and more slowly at near the centerline. Downstream, these saturation ratios plateau to a values that depend on the radial position, approximately independent of the axial coordinate. More specifically, in this example, the saturation ratio at each trajectory reaches a nearly constant value after a distance downstream of approximately 25-40 mm. Except at the walls, these plateau saturation values are greater than 1. This axial distance at which the saturation ratio plateaus scales with the flow rate and more generally the product of this axial distance and the volumetric flow rate falls in the range 0.5 to 0.8 s/cm². As noted above, the highest saturation ratios are achieved slightly off the centerline. FIG. 3B shows saturation ratios achieved for the same configuration and operating temperatures when the entering flow is perfectly dry, where 0% RH. The maximum supersaturation achieved, 1.42, is not appreciably changed from that calculated for the case when the input flow was at 50% RH.

Figure 4:
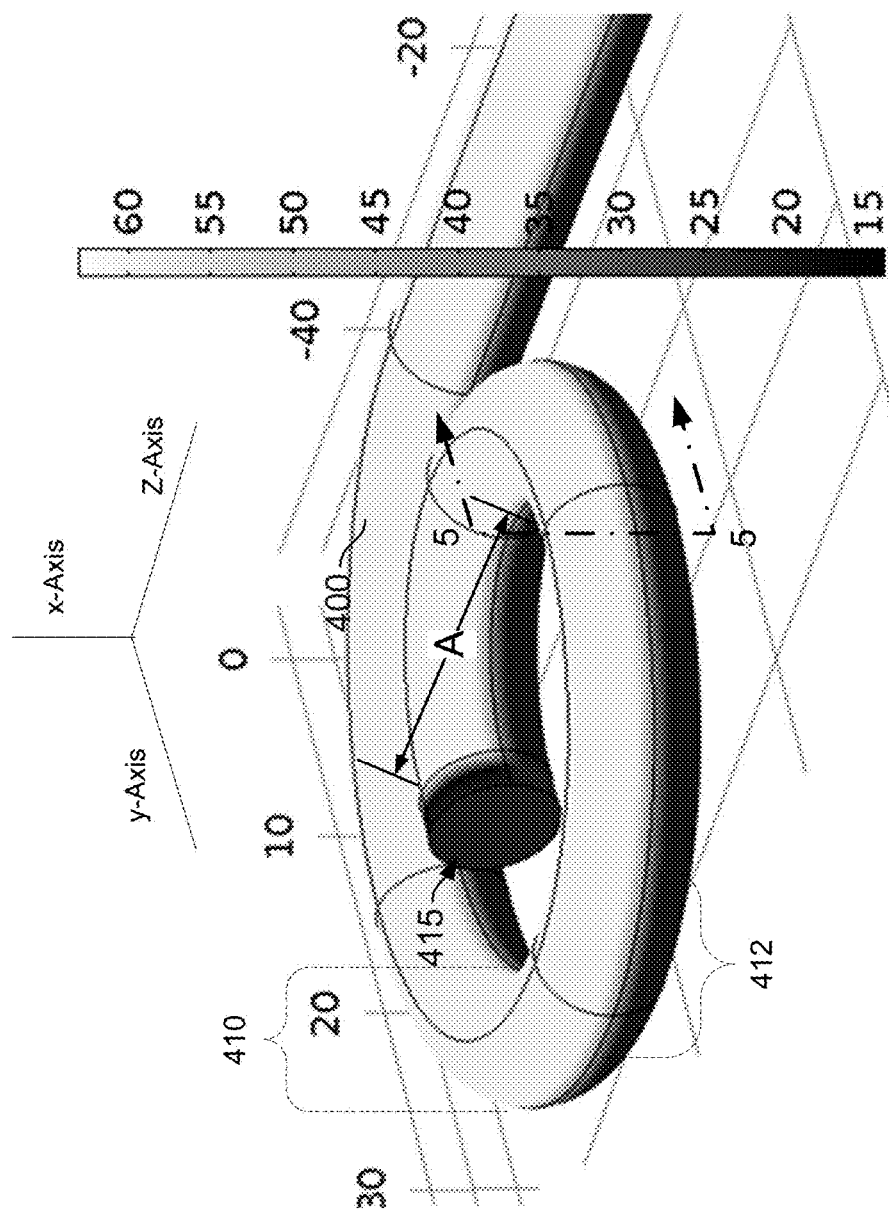

FIG. 4 illustrates a second embodiment of the present technology configured as a flat coil growth tube 400. The growth tube 400 is a coiled tube in a single plane, wherein the upper side is warmer than the underside. Air enters at the tighter radius in the center, and travels down the coil, exiting at the outer edge, as indicated by the arrows. Lighter shading indicates warmer temperatures, in accordance to the scale to the right (values in ° C.).

Although not detailed in a separate cross-section, the embodiment of FIG. 4 includes regions 410 and 412 in a manner equivalent to that of the embodiment of FIG. 1: the wall in region 410 is held at 60° C. for angular positions of roughly 20° to 160°, and the wall in region 412 is held at 20° C. for angular positions of 200° to 340° in region 112. The angular positions are relative to a common origin, and the angular positions (the origin), and hence regions 410 and 412 are constant and thereby extend longitudinally over the length of the tube 400.

In FIG. 4, the upper side 410 is warmer than the underside 412. Air enters at the tighter radius in the center at entry 415, and travels down the coil, exiting at the outer edge. Lighter shading indicates warmer temperatures, in accordance to the scale to the right (values in ° C.).

Figure 5:
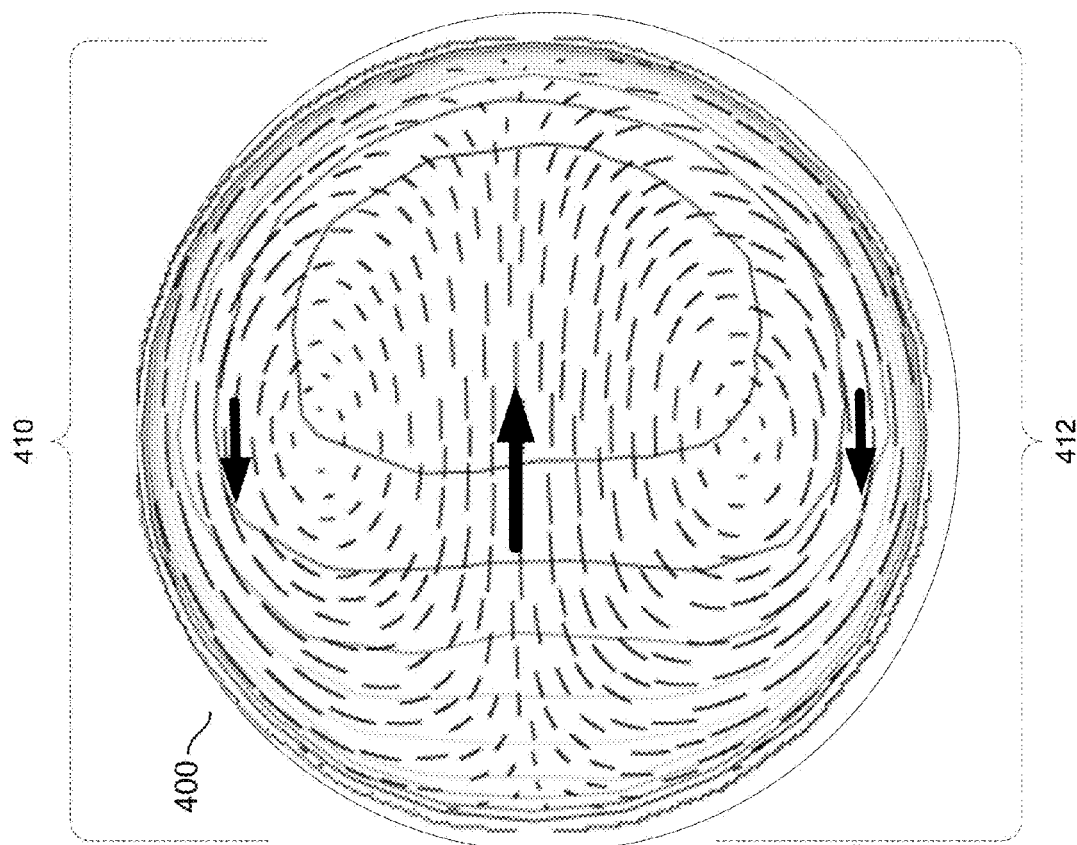
Figure 6:
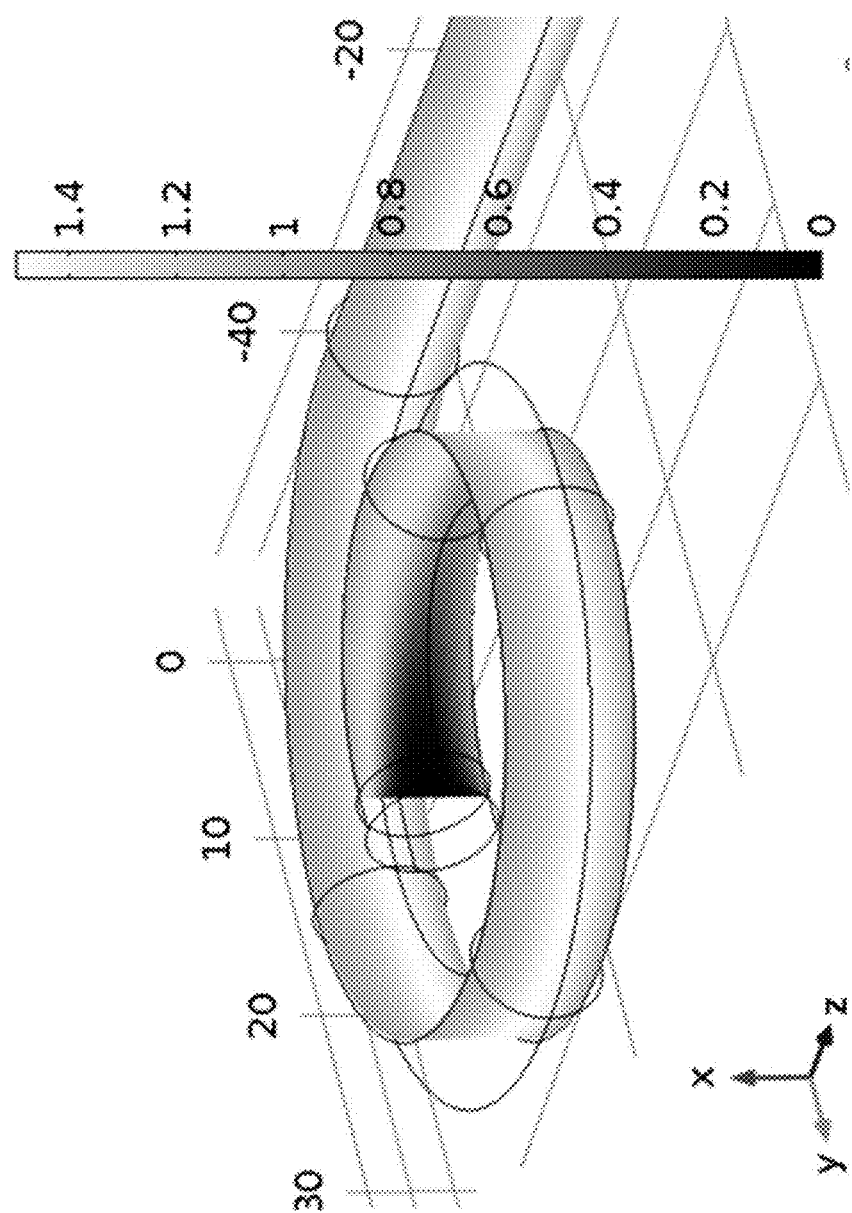

The coiled geometry leads to the development of a secondary flow pattern, as illustrated in FIG. 5. In FIG. 5, velocity fields in the coil show secondary flow patterns, where the center of the coil is to the left of the cross-section of FIG. 5. Dashed lines show the secondary flow pattern, which is the component of the flow that is perpendicular to the axis of the tube, i.e. in the plane of the paper. The length of each dash is proportional to the magnitude of the velocity. The arrows indicate the direction of the secondary flow. Solid lines are contours of constant velocity for the primary flow that travels axially down the tube. The direction of the flow for the cross section 5-5 in FIG. 4 is out of the page. As shown, the flow pattern is not turbulent; that is the flow velocity does not vary in time, it only varies spatially. However, rather than the straight flow trajectories that generally characterize laminar flow, the flow trajectories in the coiled geometry are not straight. Instead, the trajectories follow a helical pattern that brings flow from the cold and warm walls directly into the center of the flow. The center of the coil is to the left. The solid lines show the contours of equal longitudinal flow, i.e. along the axis of the tube. These longitudinal velocities are somewhat greater towards the outside of the coil. The dotted lines show the perpendicular flow components, which exhibits a double-vortex pattern. Individual flow trajectories trace double helix, with streamlines following the wall for a portion of the time, bending towards the center, and returning back to the outside.

The extent of the displacement of the longitudinal flow maximum from the center of the tube, and the magnitude of the perpendicular, vortex pattern relative to the longitudinal speeds depends on the Dean's number, defined as:

$$De = \text{Re}\sqrt{\frac{A}{D}}$$

where $$\text{Re} = \frac{\rho V D}{\mu}$$

is the flow Reynolds number, V is the mean flow velocity, D is the diameter of the tube and A is the diameter of the coil, ρ is the air density and µ the air viscosity. The coil diameter A is twice the distance from the center axis of the coil to the center of the tube. For the helical configuration A is constant, while for the flat spiral configuration A is smaller near the center of the coil. For small De<17, i.e. when the coil radius is large compared to the tube diameter, pair of symmetrically placed counter rotating vortices are formed as a result of the centrifugally induced pressure gradient. The secondary flow pattern can be described analytically as in Dravid, A. N., Smith, K. A., Merrill, E. W., Brian, P. L. T., "Effect of secondary fluid motion on the laminar flow heat transfer in helically coiled tubes," American Institute of Chemical Engineering Journal 17: 1114-1122, 1971. For moderate values, De<370, the double swirl within the tube becomes asymmetric, with higher velocities in the outer vortex, yet the flow trajectories are well defined and time-invariant. At higher De the flow begins to separate from the inner wall of the tube. The modeling presented above is for the case of De=350.

The resulting geometry is advantageous for creating vapor supersaturation needed for condensational growth as the secondary flow patterns enhance the transport of vapor from the wetted walls into the center of the flow. A parcel of air near the tube center will eventually migrate close to the wall, enhancing heat and vapor transfer. This effectively shortens the diffusional distance, and again the saturation ratio reaches a steady state value that depends primarily on radial position. Once the steady state is achieved, the saturation ratio plateaus to a nearly constant value, providing ample time for particle activation and growth.

FIGS. 6, 7A and 7B show the saturation ratios achieved with the embodiment of FIG. 5 where the coil radius R=A/2 (tube centerline measured to a 180° tube centerline) varies from 7 to 17 mm. Calculations are done for an 120 mm long tube, with a diameter of 6 mm and a volumetric flow rate of 0.3 L/min FIG. 6 illustrates the saturation ratio for a slice of the flow extending between the warm and cold surfaces of the growth tube of FIG. 4, where lighter shading indicates higher values of the saturation ratio, as shown in the scale to the right. The tube diameter D1 is 6 mm and the flow is 0.3 L/min. The condensing vapor is water, the carrier gas is air, and the entering flow is at 22° C. and 0% RH.

FIG. 7A illustrates the saturation ratio at several radial positions from the vertical slice of FIG. 4, wherein the entering flow is at 22° C. and 0% RH. FIG. 7B illustrates the saturation ratio at several radial positions from the vertical slice of FIG. 4, wherein the entering flow is at 22° C. and 50% RH. It is to be noted that this vertical slice extends from the warmer surface, through the centerline of the tube, to the colder surface, and further that it extends along the tube axis from the flow entrance to the flow exit.

The flow enters near the center at entry 415, at tighter radius of the coil. For comparison, calculations were done at the same operating temperatures, flows and tube diameters as the straight configuration of FIG. 1. The result shows the same general characteristics of the embodiment of FIG. 4 as for the straight tube embodiment of FIG. 1, although the maximum supersaturation achieved is 1.50, which is somewhat higher than the 1.42 for the straight tube. Thus the secondary flow, which brings flow from larger radial positions towards the center, enhances the supersaturation. As in the straight sandwiched growth tube approach, the maximum saturation is essentially independent of the relative humidity of the entering flow, with calculations for sampling at either 0% RH or 50% RH both giving a saturation ratio of 1.52.

A third configuration, illustrated in FIGS. 8A and 8B, is a helical coil 700. In this helical growth tube, with a spiraling coil, the inner side and outer sides of the coil are at different temperatures, as indicated by the shading. In this example the inner surface is at 60° C., and the outer one at 20° C. Carrier gas enters at inlet 720, and exits at outlet 721 This configuration can be more compact for cases when it is necessary to handle a larger sample flow rate. The example given has a tube diameter D2 of 10 mm, a coil diameter A2 of 40 mm, with an air flow rate of 7 L/min. The inner surfaces of the coil are held at 60° C. and the outer surfaces at 20° C. In FIG. 8B, the embodiment of FIGS. 8A and 8B includes regions 710 and 712 which are equivalent (though 90° rotated) to 110 and 112 in a manner equivalent to that of the embodiment of FIG. 1: the wall in region 710 is held at 60° C. for an arc length of 140°, and the wall in region 712 is held at 20° C. for angular positions of 140°, though longer or shorter arc lengths may be utilized. The angular positions are relative to a common origin, and the angular positions (the origin), and hence regions 710 and 712 occupy the same angular positions relative to the origin at each cross-section of the tube over the length of the tube 400.

FIG. 9 illustrates the saturation ratio for slice extending between the warm and cold surfaces, and passing through the centerline, of the growth tube of FIGS. 8A-8B. Lighter shading indicates higher value of the saturation ratio. Note that the saturation ratio quickly attains a value above 1.2, which is then sustained down the length of the coil. The condensing vapor is water, the carrier gas is air, and the entering flow is at 20° C. and 30% RH.

The degree of saturation achieved with this configuration is shown in the FIGS. 10. FIG. 10 illustrates the saturation ratio as a function of axial position for several radial positions for the helical sandwich configuration of FIGS. 8A-8B. In this example the maximum saturation ratio is 1.3, which is lower than achieved with the flat coil for the same operating temperatures. This lower value is likely attributed to the fact that the temperature difference is not aligned with the recirculating flow pattern, as it was in the flat coil.

The advantage of the region of sustained saturation ratio is that providing more activation time and producing large droplets, while maintaining the smaller tube diameters that are necessary to avoid degradation of the saturation at high particle concentrations due to condensational heat release.

In all of the above examples, the case of water condensation onto particles suspended in air was considered. In this instance the diffusivities of the condensing fluid and the thermal diffusivity of the carrier gas are similar, such as is the case of water condensation onto particles carried in air. The water being a small molecule diffuses more quickly than the temperature rises. Specifically the mass diffusivity of water vapor at room temperature is 0.25 $cm^2/s$ whereas the thermal diffusivity of air is 0.20 $cm^2/s$. With both heat and water diffuse from the walls into the flow, but the transport of water vapor out-paces the heat transport. The result is a region of water vapor super-saturation near the centerline.

This same approach may also be used for instances where the diffusivities or more different, such as the condensation of isopropyl alcohol onto particles in an airflow. In this case the point of trajectory of maximum supersaturation is further from the centerline of the flow than for water condensation. However, as in the examples shown, the degree of supersaturation along each trajectory reaches a nearly constant value, which provides ample time for particle activation and growth.

FIGS. 11A-11B illustrate use of the flat coiled growth tube in conjunction with a particle counter 1114*b* or as a particle collector 1114*a*. The flat coil or spiral growth tube 1120, is formed by a two symmetric plates 1105, 1107 into which a groove 1120*a* as shown in FIG. 11*c* and FIG. 11*d*. (It should be understood that an opposing and opposite groove, not shown, is cut in an upper metal plate 1105 to complete formation of the tube 1120.) These are subsequently mated together, as shown in FIG. 11*b*. A small heater 1104, such as a cartridge or film heater, is mounted on one side, and a cooler 1106, such as a Peltier or thermoelectric device, is mounted on the other. Alternatively, a single thermoelectric device can be mounted between the two plate halves 1105, 1107 to pump heat from one side to the other. Insulation between the two halves reduces the heat leak between the two plates. By using an unfired alumina bisque, or other wettable material for the construction of the two plated 1105, 1107 into which the groove is cut, it is possible to maintain wetted surfaces throughout the inner surface of the spiral. As shown, the flow enters in inlet 1102 at the center of the spiral tube 1102 and flows through the spiral, wherein the ultrafine particles grow through condensation. This growth is due to the supersaturation of vapor created by the relative rates of water and vapor transport from the wetted, non-isothermal walls, as explained above.

Figure 8B:
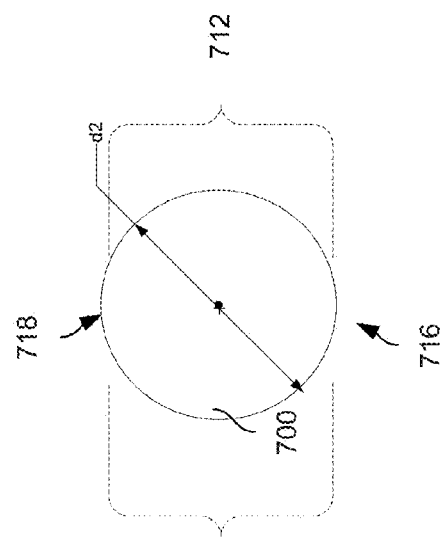
FIG. 8B is a cross-section along line 8B-8B in FIG. 8A.
Figure 8A:
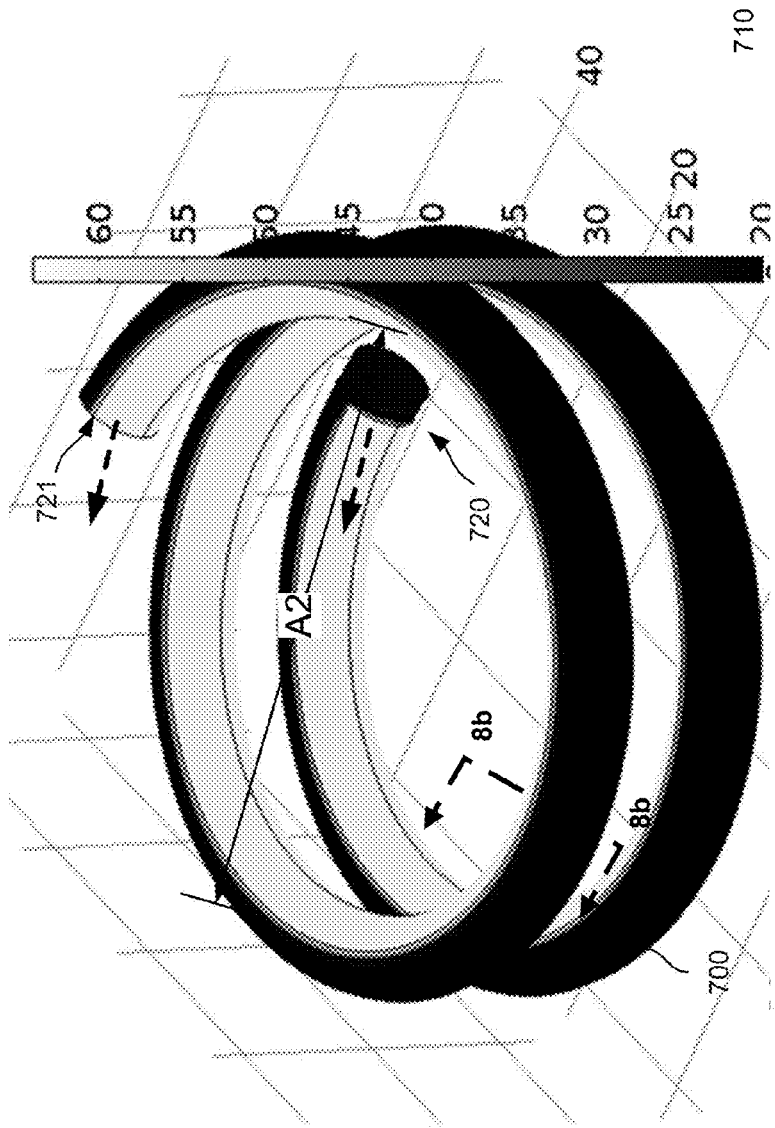
Figure 9:
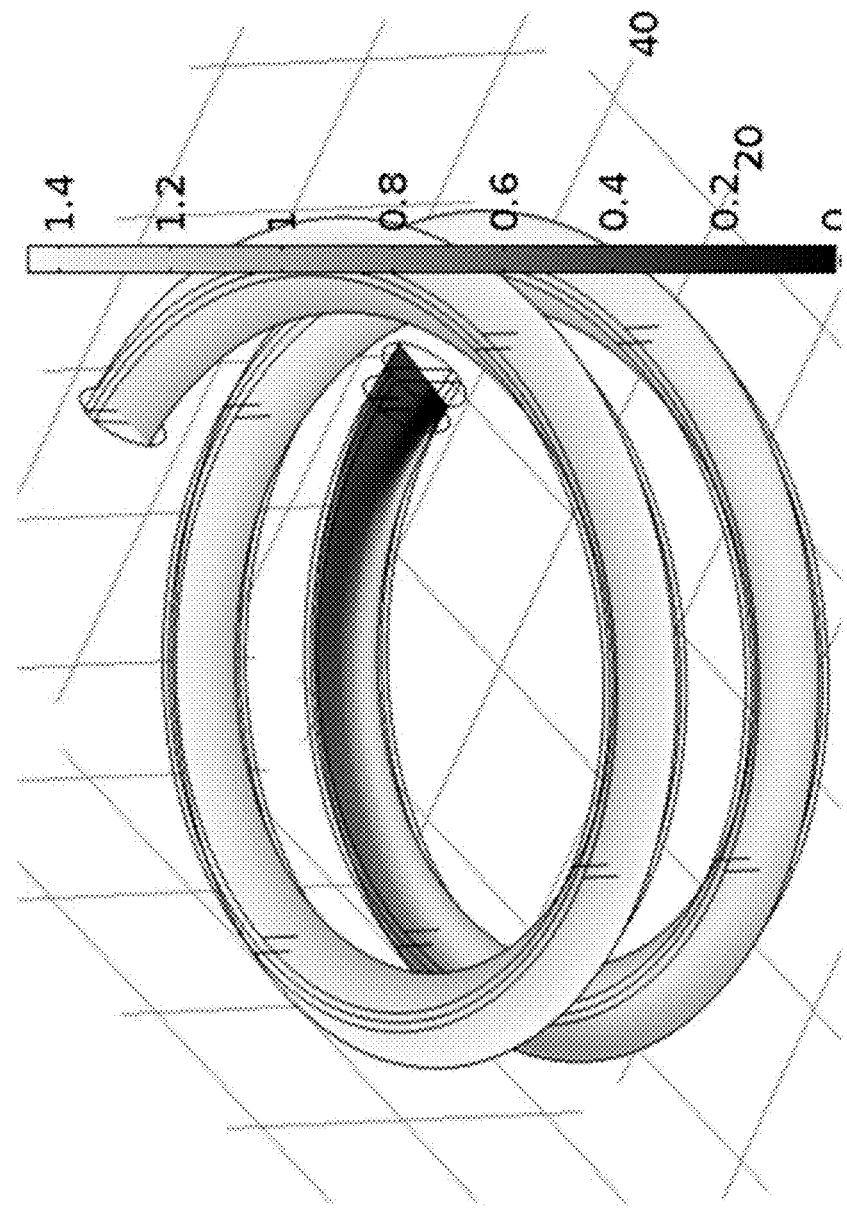
FIG. 9 illustrates the saturation ratio for slice of the flow extending between the warm and cold surfaces of the growth tube of FIG. 8A.
Figure 10:
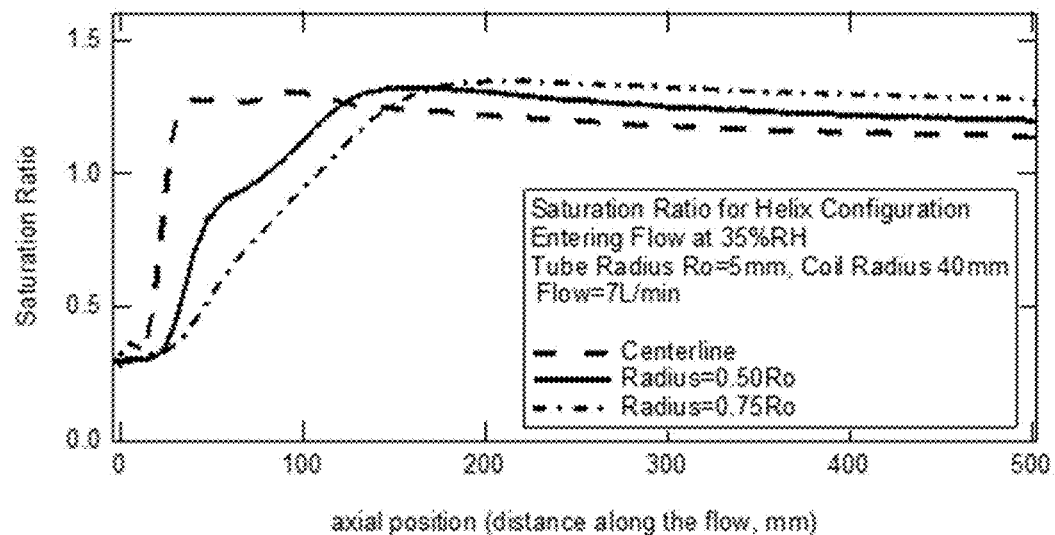
FIG. 10 is a graph illustrating the saturation ratio as a function of axial position for several radial positions for the helical configuration of FIG. 8A.
Figure 11A:
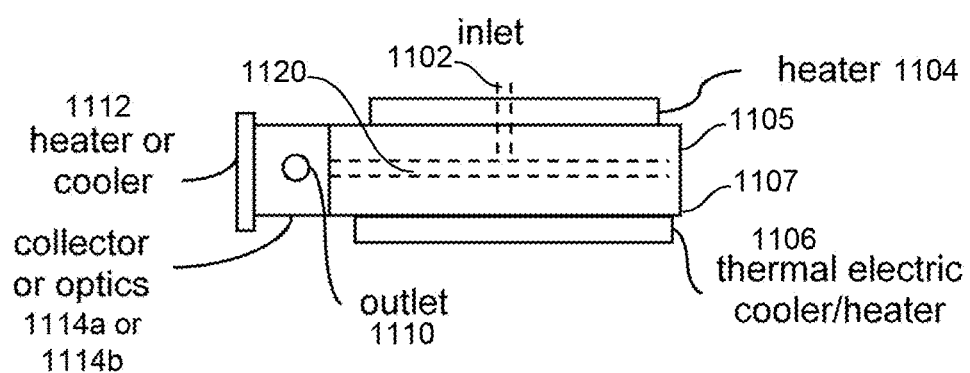
FIG. 11A is a side view illustrating a condensational growth spiral of FIG. 4A incorporated in a particle collector or a particle counter.
Figure 11B:
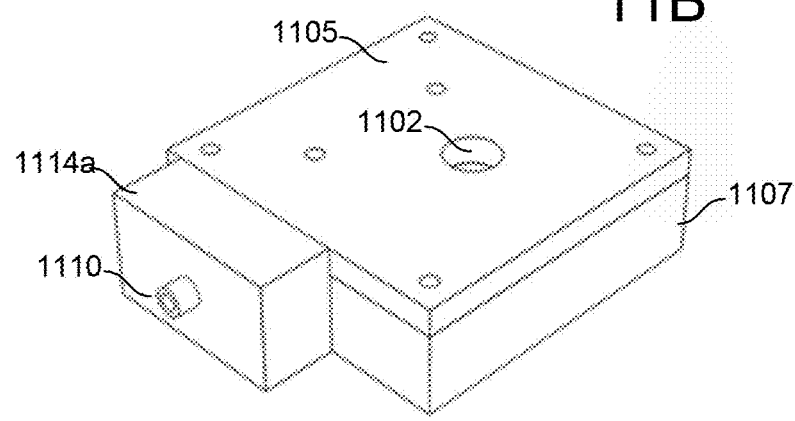
FIG. 11B is a perspective view illustrating the device of FIG. 4 configured as an optical detector with an optics head.
Figure 11C:
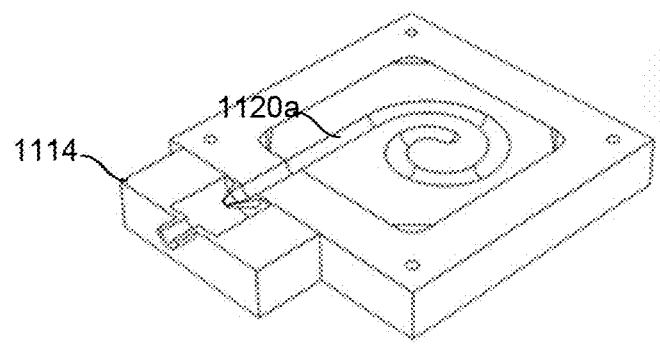
FIG. 11C is a perspective view of the device of FIG. 13B with the heating element removed.
Figure 11D:
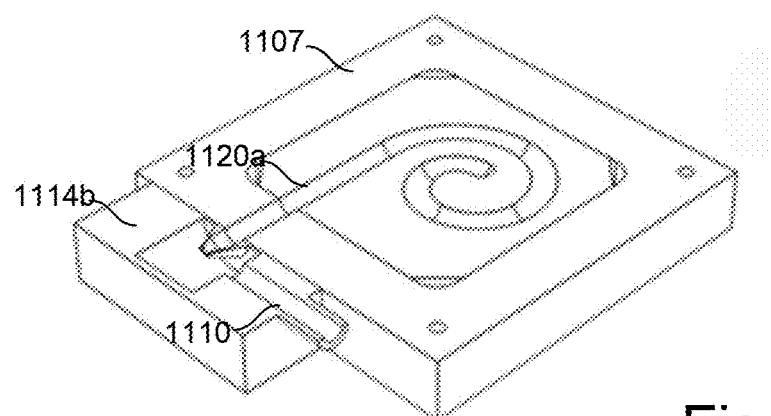
FIG. 11D is a perspective view of the device of FIG. 11A with configured as a particle collector.

Depending on the application desired, the flow is directed to an optical sensor 1114b, or to a impactor collector 1114a, as shown in FIGS. 11C and 11D. When coupled to the optical sensor 1114d, the device forms a condensation particle counter that detects and measures the concentration of individual ultrafine particles suspended in a flow of air or other gas. When coupled to an impactor collector 1114a, the device becomes an ultrafine particle collector that deposits ultrafine particles as a concentrated spot, or set of spots on a solid surface. Particle collectors can also deposit into liquid. In both applications the detection, or capture, of the ultrafine particles is enabled by the condensational growth. In addition to collection and counting, the condensational growth method presented here can be used to enhance the electrical charging, or to aerodynamically focus the particles. Although FIGS. 11A-D has illustrated these applications using the flat coil growth tube, these identical concepts also apply to the helical configuration shown in FIG. 8.

In an alternative embodiment, an insulating layer may be provided between the plates 1105 and 1107. In such embodiments, the insulating layer may be formed of plastic or foam and have a groove matching the groove in each of the plates formed therein. The resulting tube formed by the plates 1105 and 1107 with the insulating layer may not be completely circumferential (circular) but rather may have a cross-section resembling an oval shape.

The coiled approach can also be applied to the laminar flow water condensation method of Hering et al (U.S. Pat. Nos. 6,712,881 and 8,801,838) wherein flow passes in a laminar manner through a region where the walls wet and the temperature is higher than the temperature of the entering flow. It is within this warm, wet-walled section the water vapor diffuses into the cooler flow faster than it warms, creating a region of water vapor supersaturation with a maximum in the central portion of the flow. This may be preceded by a conditioning stage to regulate the temperature of the entering flow, or it may be followed by a moderating stage to extract water vapor from the flow once the supersaturation is created, or it may have all three stages operating in concert. Any of these three approaches may be adapted to the coiled approach. Due to the secondary flow patterns discussed above, the coil both enhances the rate of transport from the walls, providing a more compact design.

Figure 12:
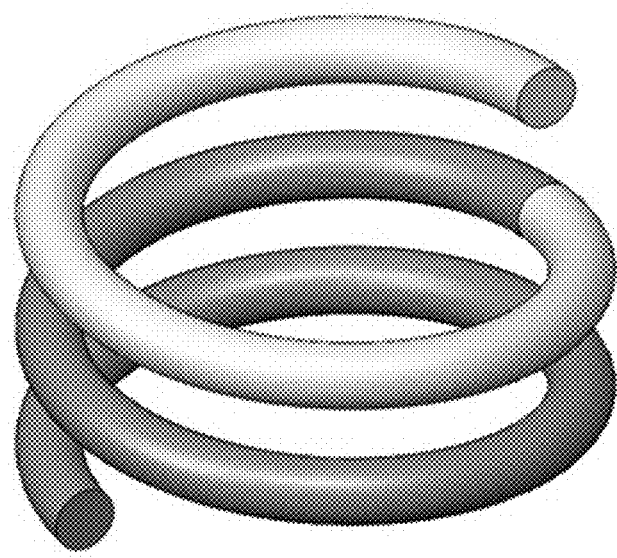
FIG. 12 is a perspective view of another embodiment comprising a coiled growth tube wherein a first portion of the spiral has circumferentially uniform colder walls than a second portion having circumferentially uniform warmer walls.

FIG. 12 shows application of the present technology to the method of U.S. Pat. No. 6,712,881 which includes a coiled growth tube with a cooled conditioner followed by a warm growth region. The air is cooled and humidified in the lower 1½ turns, and then encounters one full turn at a temperature 30° C. warmer—the growth section—during which the saturation ratio gets as high as 1.4.

Figure 13:
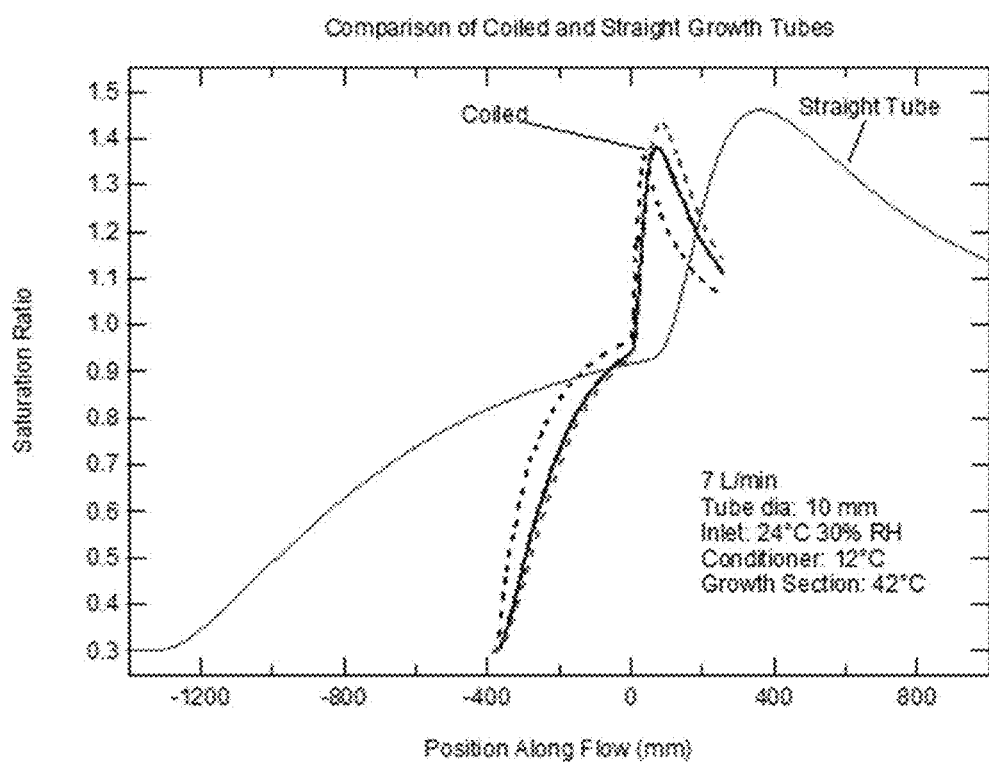
FIG. 13 is a graph illustrating a comparison between straight and coiled growth tube.

FIG. 13 illustrates a model comparison between straight and coiled growth tube. To accommodate 7 L/min, the straight version is 2 meters long. The coiled version requires substantially less tube length. FIG. 15 shows the calculated saturation ratio along the centerline for this geometry obtained through numerical modeling. These results are for a 10 mm diameter tube carrying 7 L/min of flow. FIG. 13 also compares the coiled design to the straight growth tube of that follows the method of U.S. Pat. No. 6,712,881. Both are designed to carry the same 7 L/min flow. The peak saturation ratio of the coiled tube is slightly degraded, but it accomplishes its task in less than one third of the tube length. FIG. 15 shows a side-by-side comparison of the coiled growth tube with a straight growth tube implementation. In this case, the straight version has been broken up into several parallel growth tubes, as one might do to limit the length of an instrument. The coiled version has about ⅕th the volume.

Each of the design approaches described herein utilizes variable flow rates and tube diameter components that provide non-turbulent flow in the various embodiments of the apparatus described herein. For isothermal flow in a tube, this condition can be met by selecting the tube diameter and flow such that the Reynolds number, defined above, is below as 2000. For the coiled geometry, there is an additional requirement that the Deans number is below about 500. With temperature differences, it is also necessary to select the tube diameter to ensure that the natural convection is small compared to forced convection. Natural convection refers to the flow that results from a vertical density gradient formed through a temperature difference in the system. The relative magnitude of natural to forced convection is described by the dimensionless group referred to as the Froude number, which is defined as:

$$Fr=(\rho V^2)/(\rho V_0^2)=(\rho V^2)/(\Delta \rho g L),$$

where V is the characteristic velocity for forced convection, $V_0$ is the characteristic velocity for natural (or free) convection, $\rho$ is the air density, $\Delta \rho$ is the change in air density due to temperature difference, g is the gravitational constant and L is the characteristic distance. Whereas for small Fr, natural convection dominates. For the above systems, the characteristic distance L is the axial distance over which the temperature jump occurs at the entrance, which for the examples given is the tube diameter. The systems presented above all employ small tube diameters with respect to the temperature difference such that the Fr>1. This consideration is less important if the flow is confined within a horizontal tube with the warm surface at the top, such as shown in FIGS. 1A-AB and FIGS. 4A-4B.

In summary, the advantages of a coiled geometry for enhancing the creation of a region of vapor supersaturation, and its application to condensational growth of small, airborne particles, are described herein. More specifically, it has been shown that the coiled geometry can be used in a "sandwich" configuration, wherein one side of the tube that is forms the coil or spiral is warmer than the other side. The sandwich geometry, whether coiled or not, provides for sustained high supersaturation values that can promote droplet growth even when the tube diameter is small. It also provides more time for activation of the condensational growth, a feature that can improve the initiation of growth onto less wettable particles.

Successful application of these concepts requires non-turbulent flow. For tubular geometries this criteria that is met under the conditions of Re<2000, Fr>1. In the calculations presented above the Re ranged from approximately 70 to 1000, and Fr ranged from approximately 4 to 200. It is noted however that for the flat tube configuration, with the warmer surface on top, the flow is stable will not be disrupted by buoyancy at even small values of Fr. For the coiled geometry, the literature references cited herein indicate that the Deans number should be less than 370 to prevent flow separation from the inner wall. Calculations presented above for the "snail" configuration of FIG. 4 met this criteria, with De in the range of 100-170. However, in the helical configurations of FIG. 8 and FIG. 13 calculations were done at higher De, of order of 2000-3000, as our numerical model takes into account such flow separation. Operation at higher values of De still provides enhancement of the supersaturation profile. Thus for this application that configurations with higher values of De are acceptable.

The condensational method of coiled growth tube presented above may be generalized as illustrated in FIGS. 14A and 14B. A tube 1400 of diameter D is arranged in a coil. At any point along the coil, a coil diameter A is defined as twice the distance from the central axis of the coil to the center of the tube. The tube has an inlet and an outlet through which the carrier gas is directed. Most typically, this carrier gas is air. The interior walls of the tube are wetted with a condensable fluid such as water. When viewing a cross section of the tube, the temperature along a first portion of the circumference 1410 is held to a value $T_h$, while the temperature along a second portion of the circumference 1412 is held to a value $T_c$. These two circumferential portions extend along a length of the tube. The temperature $T_h$ is higher than the temperature $T_c$, but less than the boiling point of the condensable fluid at the pressure of the flow inside the tube. The intermediate sections of the circumference 1418 and 1419 will have temperatures somewhere between $T_h$ and $T_c$. The inlet section to this growth tube may be a tubular section 1420 which is thermally insulated from the growth tube. Similarly there may be outlet section 1421 which may be thermally insulated from the growth tube. The outlet section may be a straight tube, so as to minimize inertial deposition of the droplets formed through condensational growth. It should be noted that the tube cross-section need not be completely circumferential, but may comprise a circular, oval or any arcuate surface.

The discussion above describes these circumferential portions in terms of the angular position with respect to the center axis of the tube. Calculations are presented for which the first circumferential section is described by the angular coordinates 20-160° relative to the line at the center of the tube, and the second circumferential section is described by the angular positions from around 200-340°, where these angular coordinates are relative to the center axis of the tube. In the examples given these angular positions are constant along the length of the tube. Yet it is clear that the saturation profiles, and hence the condensational growth of the suspended particles in the flow, will be substantially the same even should these angular positions vary somewhat along the length of the tube, or if the tube is not perfectly round. A slight oval shape will perform similarly. By the method presented here one expects to form regions of vapor supersaturation in any configuration where a flow is contained between two wetted surfaces held at different temperatures, and separated along a direction perpendicular to the flow.

A system using this coiled growth tube will be coupled at its outlet to a droplet measuring or manipulation device 1430 such as a particle counter, or a particle collector, or a particle focusing apparatus, or particle charger. A pump, blower or air mover 1440 may be provided. When a particle-laden flow is introduced into the system, the particles will grow by condensation onto the particles of the condensable fluid that is used to wet the walls. This condensational growth will enlarge particles as small as a few nanometers to form droplets that are a micrometer or more in diameter. The enlarged particles are much more readily counted by an optical device, or collected by an inertial device, or focused aerodynamically, or charged electrically. Thus any number of particle devices can be coupled to the outlet of the coiled growth tube to enable the measurement or manipulation of small particles more readily than would be possible without their enlargement.

Once the particles are enlarged through condensational growth, they may be more readily detected or manipulated than the original, ultrafine particle. There are many examples of application of condensational growth to enable optical detection and particles, such as used in condensation nucleus counters, or condensation particle counters. There are also many examples of the application of condensational growth to particle collection, especially for the purpose of enabling chemical or biological analyses. Condensational growth is also used to aerodynamically focus and concentrate particles, or to more efficiently charge them electrically. Any of these applications may be used with the sustained condensational growth method presented here. Indeed, the sustained condensational growth enables the formation of larger droplets, which are yet more easily detected optically, or collected inertially, or focused aerodynamically.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method of enlarging particles, comprising:

providing a coiled tube having a tube cross-section and a coil diameter, the tube includes an interior surface having an input adapted to receive a flow and an output, the tube having a length between the input and the output;

wetting the interior surface with a condensing fluid throughout the coiled tube;

heating the tube along first arcuate portion of the tube cross section in a longitudinal portion of the tube to a first temperature;

simultaneously with heating, controlling a second temperature of a second arcuate portion of the tube cross-section along at least the longitudinal portion, the second temperature being cooler than the first temperature; and introducing the flow into an interior of the tube at the input, the flow moving toward the output and through at least the longitudinal portion.

2. The method of claim 1 wherein the method includes wetting the interior surface with water.

3. The method of claim 2 wherein the tube has a circular cross-section, and the method includes heating the first arcuate cross-section of the tube in an arc length in a range of 120-160° and controllin the second arcuate cross-section of the tube in an arc length in a range of 200-340°.

4. The method of claim 2 comprising heating the first arcuate cross section and cooling the second arcuate cross-section of the tube such that the first arcuate cross-section and the second arcuate cross-section are in opposing relation about a circumference of the tube relative to an origin, the coiled tube is formed in a plane, the origin aligned in a plane through the center of the plane of the coiled tube, and heating the first arcuate cross-section having an axial position between 20 and 160° relative to the origin, and controlling the second arcuate cross-section having an axial position between 200 and 340° relative to the origin.

5. The method of claim 2 comprising heating the first arcuate cross-section and cooling the second arcuate cross-section of the tube such that the first arcuate cross-section and the second arcuate cross-section are arranged in opposing relation about a circumference of the tube relative to an origin, the coil tube is formed in a helix, the origin aligned in a plane parallel to an axis passing through a center of the helix, heating the first arcuate cross-section to form the first arcuate cross-section in an axial position between 20 and 160° relative to the origin, and controlling the second arcuate cross-section to form the second arcuate cross-section in an axial position between 200 and 340° relative to the origin.

6. The method of claim 2 wherein the step of introducing includes providing a particle laden flow at a temperature of about 20-25° C.

7. The method of claim 1 wherein heating comprises heating the first arcuate cross-section to a temperature of about 60° C.

8. The method of claim 1 wherein cooling comprises controlling the second arcuate cross-section to a temperature of about 20° C.

* * * * *

UNITED STATES PATENT AND TRADEMARK OFFICE
CERTIFICATE OF CORRECTION

PATENT NO. : 10,252,237 B2
APPLICATION NO. : 14/886661
DATED : April 9, 2019
INVENTOR(S) : S. Hering et al.

Page 1 of 1

It is certified that error appears in the above-identified patent and that said Letters Patent is hereby corrected as shown below:

In the Claims

Column 12, Line 33 (Claim 1), please change "along first" to -- along the first --.
Column 12, Line 49 (Claim 3), please change "controllin" to -- controlling --.

Signed and Sealed this
Eighth Day of September, 2020

Andrei Iancu
*Director of the United States Patent and Trademark Office*